United States Patent [19]
Triner et al.

[11] Patent Number: 5,936,353
[45] Date of Patent: Aug. 10, 1999

[54] HIGH-DENSITY SOLID-STATE LIGHTING ARRAY FOR MACHINE VISION APPLICATIONS

[75] Inventors: James E. Triner, Gates Mills; Steven D. Cech, Aurora, both of Ohio

[73] Assignee: Pressco Technology Inc., Solon, Ohio

[21] Appl. No.: 08/627,211

[22] Filed: Apr. 3, 1996

[51] Int. Cl.$^6$ .............................. G01N 21/84; H01L 33/00
[52] U.S. Cl. ...................... 315/112; 250/559.04; 257/717
[58] Field of Search ............................... 315/112; 257/88, 257/99, 717; 250/559.04, 559.16, 559.17

[56] References Cited

U.S. PATENT DOCUMENTS

| | | |
|---|---|---|
| 3,711,789 | 1/1973 | Dierschke. |
| 3,964,014 | 6/1976 | Tehon. |
| 4,728,999 | 3/1988 | Dannatt et al.. |
| 4,882,498 | 11/1989 | Cochran et al. ............ 250/559.04 |
| 4,896,168 | 1/1990 | Newman et al.. |
| 5,113,232 | 5/1992 | Itoh et al.. |
| 5,121,146 | 6/1992 | Smith et al.. |
| 5,173,839 | 12/1992 | Metz, Jr.. |
| 5,218,383 | 6/1993 | Kondou et al.. |
| 5,278,432 | 1/1994 | Ignatius et al.. |
| 5,362,986 | 11/1994 | Angiulli et al. ............... 257/723 |
| 5,390,093 | 2/1995 | Himeno et al.. |
| 5,479,029 | 12/1995 | Uchida et al. ................ 257/81 |

FOREIGN PATENT DOCUMENTS

| | | |
|---|---|---|
| 61-135171 | 6/1986 | Japan. |
| 62-235787 | 10/1987 | Japan. |
| 4-18771 | 1/1992 | Japan. |
| 5-218510 | 8/1993 | Japan. |

OTHER PUBLICATIONS

Heidrich et al., "LED Array Print Head Configuration", IBM Technical Disclosure Bulletin, vol. 25, No. 7A (Dec. 1982).

Hewlett–Packard Co. (SnapLED), Photonics Spectra (May 1997).

*Primary Examiner*—Don Wong
*Assistant Examiner*—David H. Vu
*Attorney, Agent, or Firm*—Fay, Sharpe, Beall, Fagan, Minnich & McKee

[57] ABSTRACT

A solid-state lighting unit for automated visual inspection includes a high-density array of light emitting diodes. The packing density of said diode array being limited only by the physical size of the light emitting diode chips and the ability to perform die and wire bond operations on the bare chips. Each diode is disposed on an electrically insulated, thermally conductive base unit. The base unit is, in turn, in a thermally conductive path with a heat dissipator. The provisions made to ensure a thermally conductive path from the individual light emitting diode chips to the heat dissipator combined with the high chip packing densities work together to create a solid-state lighting array capable of producing extremely high illumination fields when operated in either pulsed or continuous current mode.

37 Claims, 4 Drawing Sheets

HIGH-DENSITY SOLID-STATE LIGHTING ARRAY FOR MACHINE VISION APPLICATIONS

BACKGROUND OF THE INVENTION

This application pertains to the art of illumination systems used in connection with automated visual inspection systems and will be described with reference thereto. However, it will be appreciated that the invention has broader applications, such as in the provision of an extremely reliable and uniform lighting system for any application requiring controlled illumination.

Machine vision continues to obtain increasing significance in industry to aid in robotic assembly systems as well as inspection systems for product sorting or quality control. Such machine vision systems are comprised generally of a lighting system to illuminate a specimen and a camera for capturing light reflected therefrom. A digitized image is formed from the light received by the camera.

More recently, implementations of configurable, solid-state lighting arrays and machine vision systems have improved significantly overall performance levels and quality in such systems. See, for example, U.S. Pat. No. 4,882,498 to Cochran et al., commonly owned by the assignee hereof and incorporated herein by reference.

While initial techniques for forming solid-state lighting arrays provided significant improvement over earlier lighting systems, they nonetheless provided some limitations in obtainable total light output intensity, as well as being expensive to fabricate. These concerns are particularly significant in applications employing large lighting arrays, such as required for inspecting materials provided in a continuous web format, such as textiles, films, paper, metals, and the like.

Configurable solid-state lighting arrays are presently fabricated using individually packaged LED components. In such a construction, an individual light emitting p-n junction chip is typically encapsulated in a transparent epoxy. The epoxy acts to mechanically support the sensitive diode. Additionally, the epoxy capsulation is often molded into a spherical shape, thus giving it some lensing action. The lens-like characteristics of the epoxy encapsulation effectively concentrates the broad angular distribution of light emitted by a diode junction into a limited cone angle.

Such LED construction is often useful in applications in which the device is used as a panel or circuit board indicator. However, in machine vision applications wherein it is desirable to generate a uniform illumination pattern over a broad spatial field, the tendency of a lensed LED to generate illumination "hot spots" is deleterious.

Earlier attempts to address the hot spot problem have employed such means as diffusers disposed between LEDs and a target, or with an increase of a distance between the LED light source and the target.

Yet another draw back inherent to conventionally fabricated solid-state lighting arrays is the relatively large physical space requirement for epoxy packaging. A typical light emitting surface of a p-n junction is approximately 0.010 inches square. This small junction is usually encapsulated in a package with a diameter ranging from 0.10 inches to 0.25 inches. Thus, the ability to pack individual LEDs together into an array is constrained to a large degree by the packaging of the individual LED devices themselves.

Yet another disadvantage of illumination sources employing individually packaged LEDs is provided by virtue of the fact that the epoxy material in which they are encapsulated is a poor heat conductor. An important factor which limits the amount of light which may be emitted from an LED is the surface temperature of the associated emitting p-n junction. As surface temperature increases, the current-to-light-conversion efficiency of the device decreases correspondingly. Additionally, as the drive current of a device is increased, the power dissipated by the LED in the form of heat also increases. This tends to raise the surface temperature of the p-n junction. Thus, conventional LEDs are self-limited in the amount of light which they can generate.

The subject invention overcomes the above problems, and others, providing a dense array of solid-state light emitting diodes capable of providing an extremely high light output.

THE SUMMARY OF THE INVENTION

The present invention contemplates a new and improved machine vision inspection illumination system which overcomes all of the above-referred problems, and others, and provides solid-state illumination less expensively and with higher light output and improved lighting uniformity.

In accordance with the present invention, there is provided a high-density, solid-state lighting array which includes a dense array of semiconductor LEDs that are incorporated onto an electrically insulative, thermally conductive base portion. A heat dissipator is disposed in a thermally conductive path with the base portion so as to quickly communicate heat away from the LEDs.

In accordance with a more limited aspect of the present invention, the heat dissipating mechanism includes a thermal electric module which is suitably provided with a finned heat sink.

In accordance with another aspect of the present invention, the electrically insulative, thermally conductive base portion is comprised of at least one of beryllium oxide, aluminum oxide, and an insulated metal substrate.

In accordance with a yet more limited aspect of the present invention, a lens or window is provided between the lighting array and an associated specimen to direct and/or homogenize light resulting therefrom.

An advantage of the present invention is the provision of a solid-state lighting system which is particularly suited to automated machine vision systems.

Yet another advantage of the present invention is the provision of a solid-state illumination system which generates a high light output from a relatively inexpensive array.

Yet another advantage of the present invention is the provision of a solid-state illumination system which provides extremely uniform light output.

Further advantages will become apparent to one of ordinary skill in the art upon a reading and understanding of the subject specification.

BRIEF DESCRIPTION OF THE DRAWINGS

The invention may take physical form in certain parts, and arrangements of parts, a preferred embodiment of which is described in detail in the specifications and illustrated in the accompanying drawings which form a part hereof, and wherein.

DETAILED DESCRIPTION OF THE PREFERRED EMBODIMENT

Figure 1:
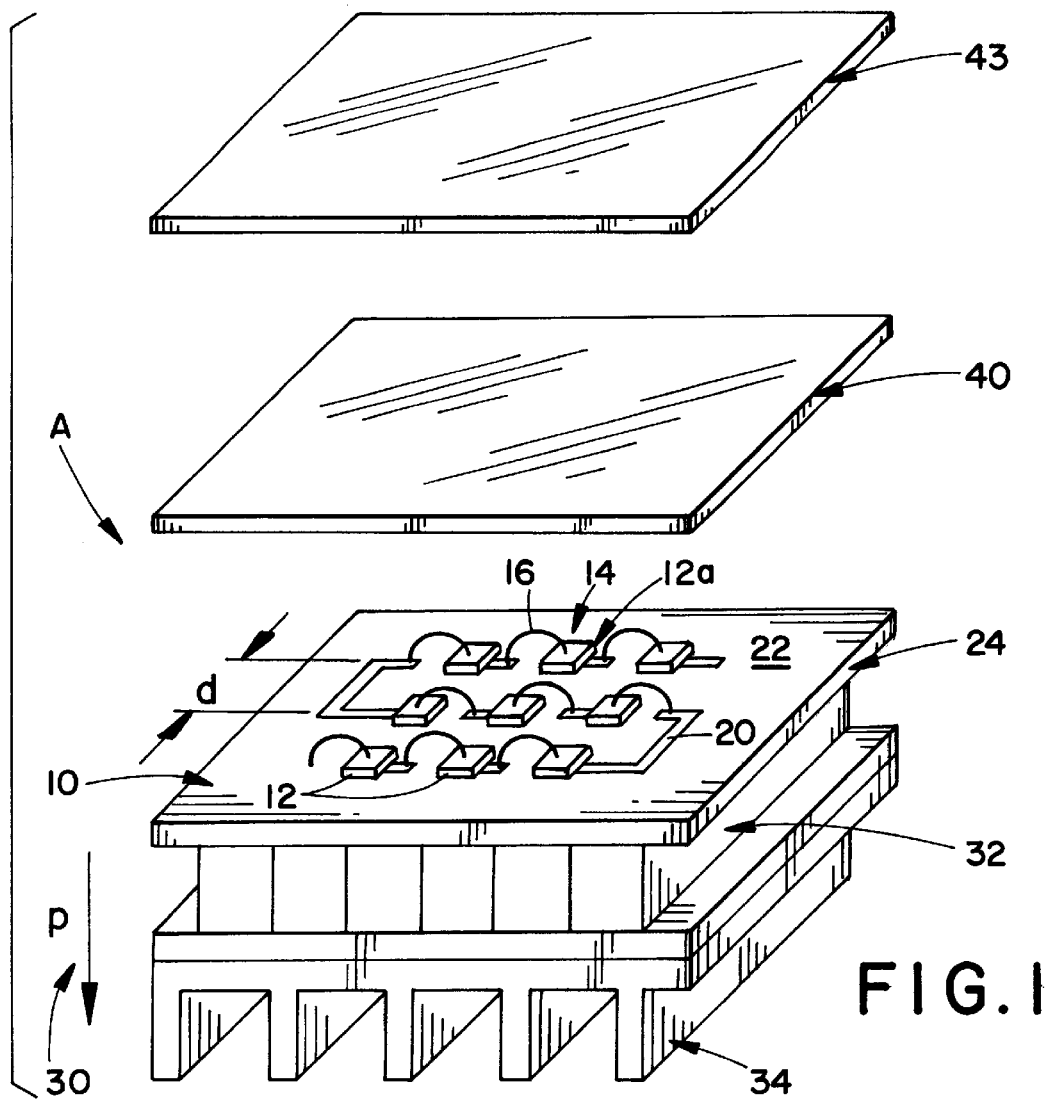
FIG. 1 provides a perspective view of a solid-state illumination assembly in accordance with the present invention.

Turning now to the drawings wherein the figures are for the purpose of illustrating the preferred embodiment of the invention only, and not for the purpose of limiting the same, FIG. 1 illustrates a preferred embodiment of a high-density solid-state lighting array of the subject invention. The array A includes a base portion 10 comprised of an electrically-insulative, thermally-conductive material. Several high thermal conductivity substrates are advantageously used to form the base portion 10. Suitable materials include beryllium oxide (BeO), aluminum oxide ($Al_2O_3$), as well as insulated metal substrates (IMS) or graphite substrates. BeO and $Al_2O_3$ are ceramic compounds which provide good thermal conductivity combined with relatively poor electrical conductivity. Indeed, the substrate is selected for its ability to facilitate the conduction of locally generated thermal energy away from the lighting array while at the same time provide electric isolation to support parallel and series circuitry associated with the lighting array. IMS are composite materials which are comprised of a high thermal conductivity metal structure (such as copper, aluminum, or stainless steel) combined with a thin layer (about 0.003 inches thick) of ceramic film. Such ceramic film provides an electrically insulting layer upon which LED devices are secured, such as will be detailed below.

Typical thermal conductivity values for several of the substrate materials which are suitable for use in connection with the subject invention are presented below.

| MATERIAL | THERMAL CONDUCTIVITY (W/M · ° K.) |
| --- | --- |
| BeO | 220.3 |
| $Al_2O_3$ | 29.8 |
| Copper | 398 |
| Aluminum | 205 |
| $H_2O$ (reference) | .60 |
| FR-4 (standard printed circuit board) | .26 |

In the illustration of FIG. 1, the generally-planar base portion 10 has several light emitting elements in the form of light emitting diodes (LEDs) 12 disposed on a single surface thereof. The LEDs emit light when electrically forward biased. In the illustration, each of the LEDs 12 is formed of a semiconductor compound and has an associated p-n junction, a representative one of which is illustrated generally at 14. The selected semiconductor compound used to form the LEDs 12 has the property of directly converting a percentage of the electrons which are conducted through their volume into emitted photons in the UV, visible, and/or IR portions of the electromagnetic spectrum. The selected compound could comprise AlGaAs, AlInGaP, GaP, GaAs, and/or GaN. The p-n junction is disposed between a conductor such as 16 and each semi-conductor, a representative of which one is provided at 12a. A spacing d, which is approximately 0.05" (inches) in a preferred embodiment of the invention, is provided between rows of LEDs 12, which distance is chosen to maximize the optical output power of the LED array. The particular distance d is highly application specific and is contingent upon the particulars chosen for the fabrication of the array. Common power conductors, exemplary shown at 20, are suitably disposed on the surface of the base portion 10 to provide electrical connections to each of the LEDs 12.

As noted above, all LEDs 12 are suitably fabricated on a single surface 22 of the base portion 10 in the lighting array or pattern. At high packing densities, such as the high density of the preferred embodiment (0.05" apart), management of the ancillary thermal energy generated during operation of the lighting array becomes one of the main issues governing the successful use of solid-state lighting arrays for general lighting applications. So, in the preferred embodiment, an opposite surface of the base portion 10, located at 24, is disposed adjacent to and in a thermally-conductive path to a heat dissipator, illustrated generally at 30, to reduce the temperature of the LEDs within the array. In the preferred embodiment, the heat dissipator 30 is an active heat reservoir capable of freely exchanging thermal energy with the ambient environment and includes a thermal-electric cooler 32 and a finned heat sink 34. Forced air is used to facilitate the thermal transfer of energy from the finned heat sink to the ambient environment.

Figure 2:
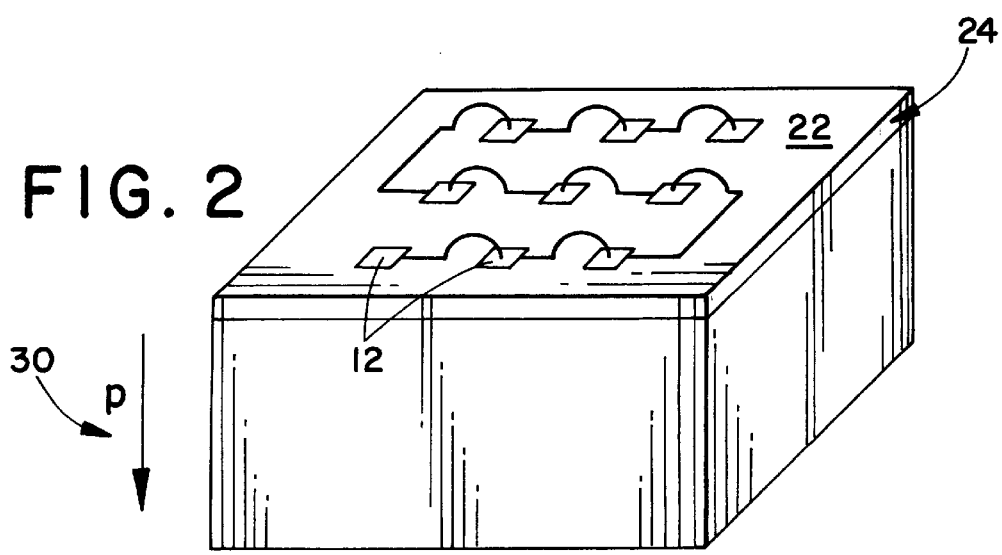
FIG. 2 shows an alternative embodiment of the array of the present invention.

FIG. 2 shows a structure representative of alternatives for the heat dissipator 30. For example, the heat reservoir could be a cavity-filled structure capable of supporting fluid flow which, in turn, facilitates thermal transfer of energy from the heat reservoir to the ambient environment. It will further be appreciated that various other active and passive cooling devices are suitably implemented as the heat dissipator 30. For example, re-circulated water, Carnot cycle coolers, Stirling cycle coolers, thermo-electric coolers, and refrigerated water chillers and other active cooling components are suitably implemented.

Referring again to FIG. 1, application of electric current to the thermal-electric module 32 provides for conduction of heat from the base unit 10, through its second surface 24, to the finned heat sink 34. Thus, substantial amounts of heat may be quickly conducted away from the LEDs 12, which are relatively densely packed. Operating in this fashion, the emitting diodes can potentially be driven to temperatures below the ambient air temperature. In the preferred embodiment, chip packing density is advantageously in the order of 400 LEDs per square inch.

Also illustrated in FIG. 1 is a thermal conductivity path p, which evidences flow of heat from the LEDs 12, through the thermal-electric cooler 32, to the finned heat sinks 34. The thermal conductivity path p is also shown in FIG. 2.

A translucent window 40 is advantageously disposed adjacent to the array. Three lensing options are contemplated, each of which is particularly advantageous for specified illumination applications.

Figure 3:
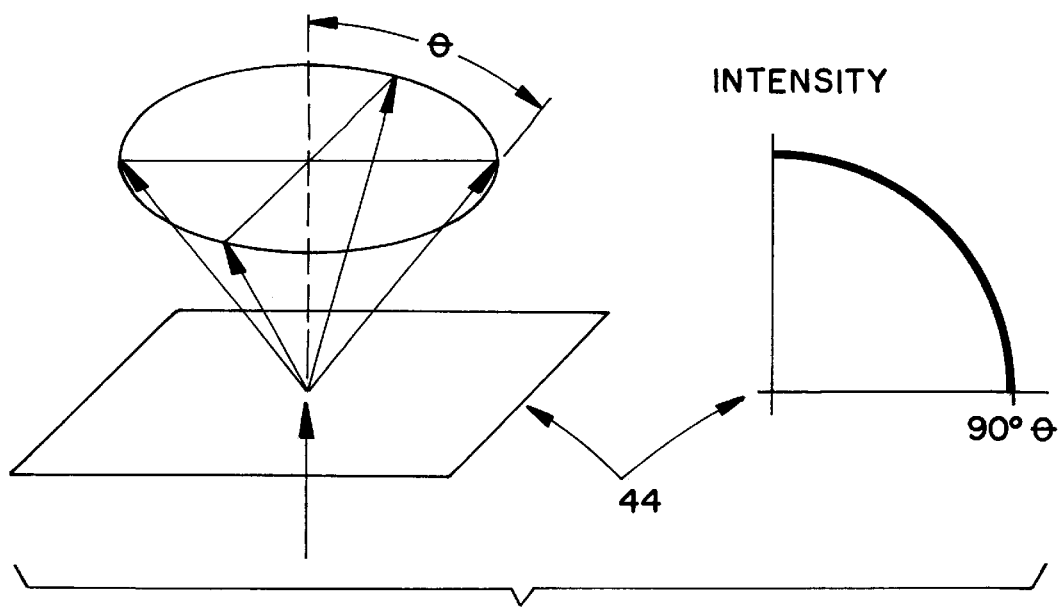
FIG. 3 illustrates generally a Lambertian-type diffuser element.
Figure 4:
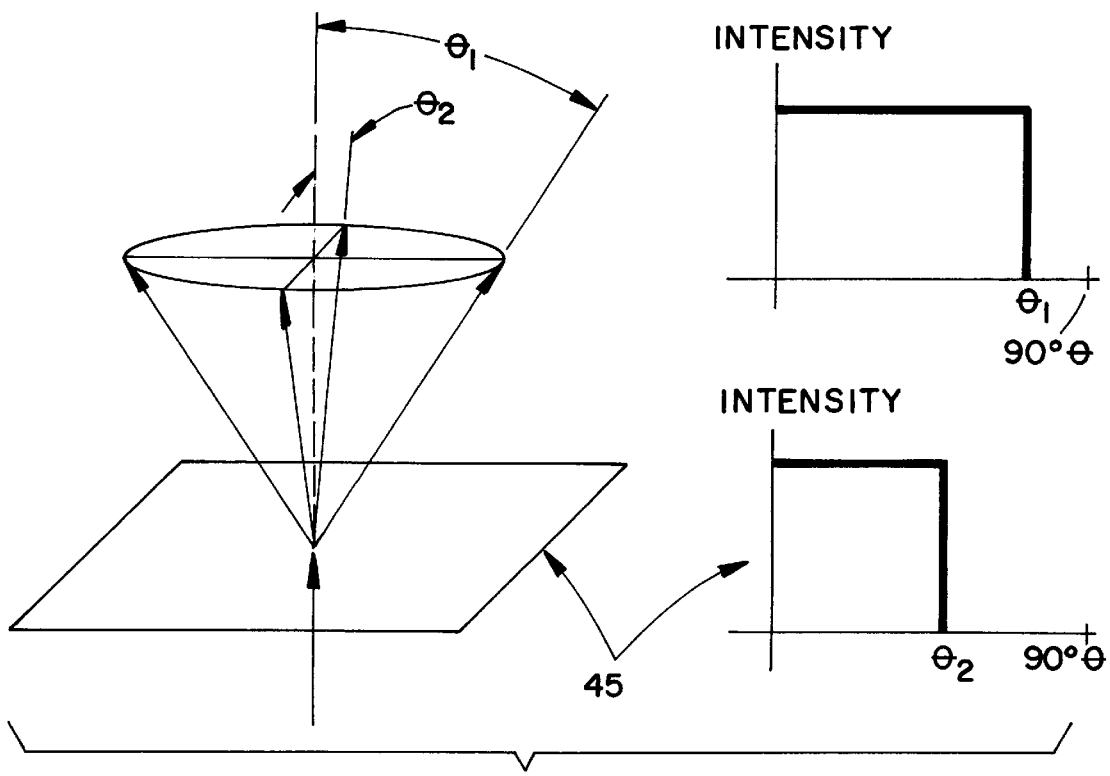
FIG. 4 illustrates generally a diffractive-type diffuser element.

In a first option, raw un-focussed radiation fields produced by LEDs 12 of the array are available for specified applications. That is, the optical radiation emitted by the device may be used in either transmission or reflection within systems performing online process control and/or machine vision inspection applications. Parameters such as intensity, illumination geometry, spectral content, angular distribution, and relative uniformity may be controlled to optimize the illumination for a particular machine vision inspection or process control application. Moreover, a diffuser element generally, representatively shown at 43 may be employed to direct the emitted radiation to a preselected area, as those skilled in the art will appreciate. For example, the diffuser element may be a Lambertian-type diffuser 44 (ground glass, etc.), as shown in FIG. 3, or a diffractive-type diffuser 45, as shown in FIG. 4, capable of generating either circular or elliptical illumination patterns. FIGS. 3 and 4 also show graphs of intensity versus the angle θ to illustrate operational characteristics of the respective diffusers.

Figure 5:
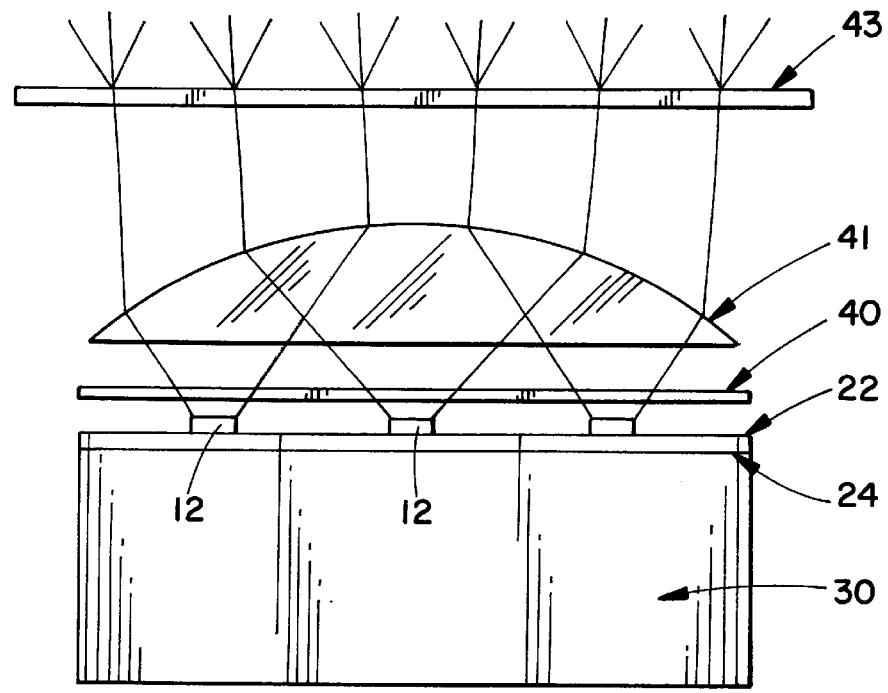
FIG. 5 shows an alternative embodiment of the present invention.

In a second option, as illustrated in FIG. 5, a macro lens 41 is suitably used to manipulate the complete radiation field emitted by the array to direct the light as a whole to a preselected area. By way of example, a cylindrical lens can suitably be located over top of the entire array. Preferably, the macro lens utilizes one or more of refraction, reflection, and diffraction to induce desired lensing action. In addition, as with the first lensing option, a diffuser element generally shown at 43 may be used to direct emitted light to a preselected area. For example, the diffuser element may be a Lambertian-type diffuser 44 (ground glass, etc.) (FIG. 3) or a diffractive-type diffuser 45 (FIG. 4) capable of generating either circular or elliptical illumination patterns.

Figure 6:
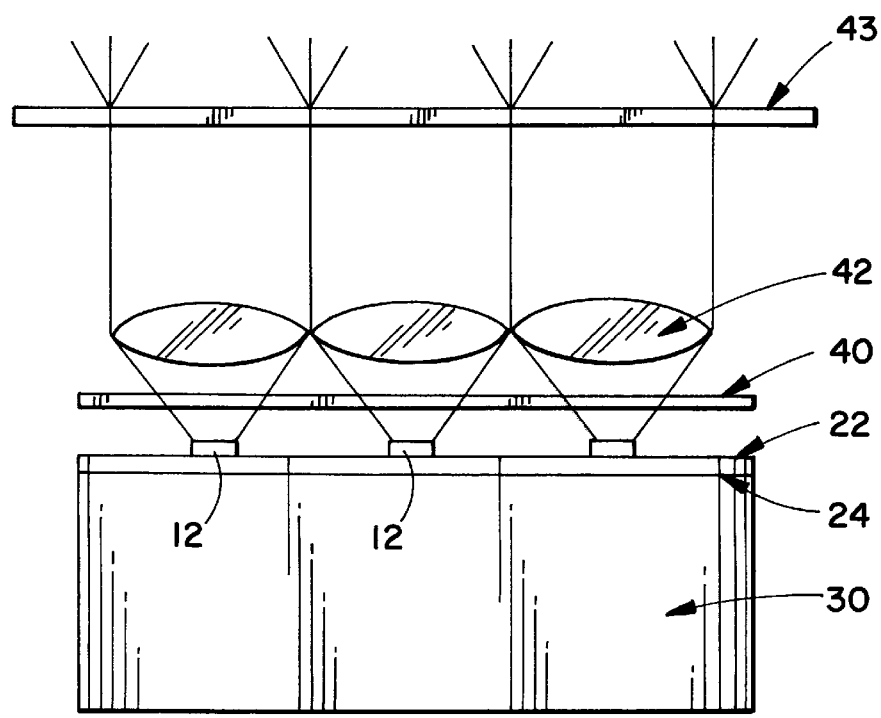
FIG. 6 shows an alternative embodiment of the present invention.

Referring now to FIG. 6, a third lensing choice for use with the translucent window 40 is a plurality of lenses arranged as a lenslet array 42 to direct light generated by each of the LEDs 12 to a preselected area. The lensing action of such a lenslet array is suitably refractive, reflective, diffractive, or a combination of methods, the choice being highly application specific to induce a desired lensing action. Various lenslet arrays are well known in the art and available in the marketplace. Again, a diffuser element generally shown at 43 may be used to direct light to a preselected area. For example, such a diffuser element may be a Lambertian-type diffuser 44 (ground glass, etc.) (FIG. 3) or a diffractive-type diffuser 45 (FIG. 4) capable of generating either circular or elliptical illumination patterns.

It will be appreciated that various wiring schemes, such as parallel or serial configurations, may be utilized among the LEDs 12. This provides for a high degree of selective configureability of the LED array during the design process.

Figure 7:
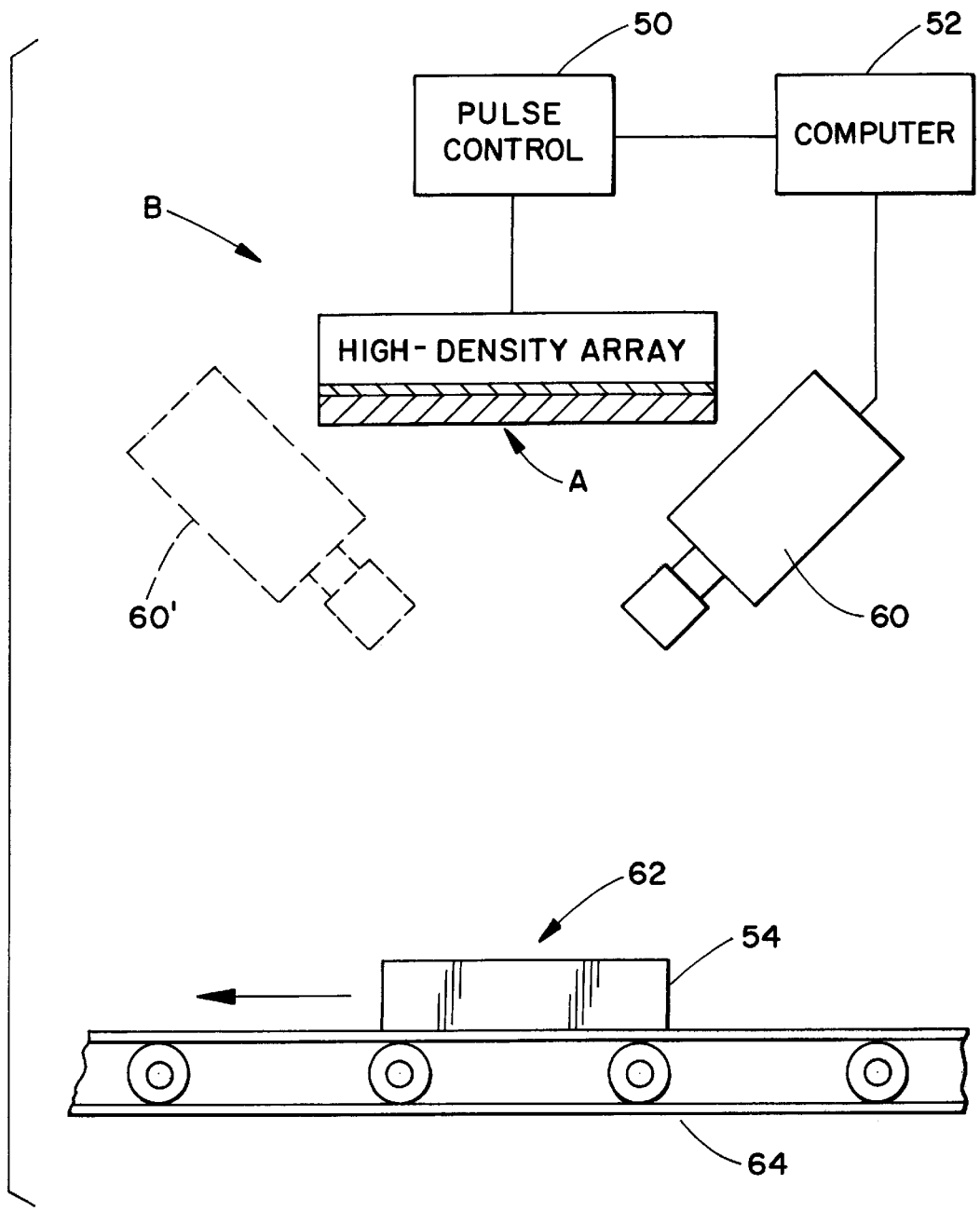
FIG. 7 is a schematic diagram of a video inspection system employing the solid-state illumination array of the subject invention.

Turning now to FIG. 7, an example inspection system B employing the high-density solid-state lighting array A of FIG. 1 is provided. The system B includes a lighting control unit 50 which provides selected drive current and/or pulse duration and rate parameters to the array A.

In a pulsed-current mode, such as that advantageously used for freezing images, pulse duration and period and pulse current are electronically configurable. The lighting control unit 50 provides pulsed current to LEDs of the array A. A suitable range of such pulsed current is 0.1 amp up to 10 amps. The lighting control unit 50 also controls the pulse duration and duty cycle, or period, of array A. Pulse durations are suitably in the range of 1 to 1000 μsec. In addition, a suitable duty cycle or ratio of off-time to on-time is in the range of 2:1 to 1000:1, with 300:1 being a typical operation condition. In addition, different geometric areas within the array may be independently addressable as a function of current level and pulse duration. In one embodiment, the LEDs all emit optical radiation of essentially the same limited wavelength range so that the control unit 50 provides a configurable intensity and geometry functionality which can be utilized to optimize the emitted radiation fields for a given application area. In a second embodiment, LEDs of two or more emission wavelengths are disposed in the array such that the control unit 50 will provide to the array a configurable intensity, geometry, and spectral content functionality to be utilized to optimize the emitted radiation fields for a given application area.

In a continuous mode, the drive current to the LEDs is an electronically configurable parameter and the lighting control unit 50 provides controlled continuous current to the individual LED's in the range of 1 to 200 mA. In addition, different geometric areas within the array may be independently addressable as a function of current level. In one embodiment, the LEDs all emit optical radiation of essentially the same limited wavelength range so that the control unit 50 provides a configurable intensity and geometry functionality which can be utilized to optimize the emitted radiation fields for a given application area.

The lighting control unit 50 operates under the direction and control of a suitable computer system 52. A camera or image acquisition means is illustrated generally at 60. It will be appreciated, however, that additional cameras, such as that 60', are also suitably utilized. Camera or cameras 60 are trained onto an inspection area 62 which is selectively illuminated by the array A under control of the lighting control unit 50 and the computer 52. Images of a specimen 54 disposed in the illumination area 62 are acquired by the camera or cameras. Such images are communicated to the computer system 52 for analysis. From the illustration, it will be appreciated that a series of specimens 24 may be selectively or serially communicated to the viewing area 62 by moving them along a conveyor 64, or the like.

This invention has been described with reference to the preferred and alternate embodiments. Obviously, modifications and alterations will occur to others upon the reading and understanding of the specification. It is intended that all such modifications and alterations be included insofar as they come within the scope of the appended claims or the equivalents thereof.

Having thus described the invention, we now claim:

1. A machine vision apparatus comprising:
   a lighting array for selectively illuminating a viewing area comprising,
   a plurality of individual light emitting elements formed of a semiconductor compound which directly converts a percentage of electrons which are conducted through their volume into emitted photons in one of UV, visible, and/or IR portions of an electromagnetic spectrum, the light emitting elements being placed within a one- or two-dimensional pattern wherein element spacing is less than or equal to 0.05",
   an electrically insulative, thermally conductive support substrate having a thermal conductivity greater than 1 W/m•°K upon which the light emitting elements are directly attached in formation of the pattern, said support substrate specifically selected for its ability to facilitate conduction of locally generated thermal energy away from the light emitting elements while at the same time providing a sufficient degree of electrical isolation required to support parallel and series circuit construction associated with the individual light-emitting elements, and,
   a heat dissipater disposed in direct thermal contact with the thermally conductive support substrate reducing the temperature of the light-emitting elements within the array;
   a camera for acquiring images of specimens disposed in the illuminated viewing area;
   a lighting control unit in communication with the lighting array; and,
   a computer in communication with the camera to receive the acquired images and in communication with the lighting control unit.

2. The apparatus of claim 1 wherein the electrically insulative, thermally conductive substrate is comprised of at least one of beryllium oxide (BeO), alumina ($Al_2O_3$), insulated metal substrate and graphite substrate.

3. The apparatus of claim 1 wherein the semiconductor compound is comprised of one or more of the following chemical compounds: AlGaAs, AlInGaP, GaP, GaAs, and GaN.

4. The apparatus of claim 1 wherein the heat dissipator is comprised of at least one of a Carnot-cycle cooler, a Stirling-cycle cooler, thermo-electric cooler, and a refrigerated water chiller.

5. The apparatus of claim 1 wherein the heat dissipator is an active heat reservoir freely exchanging thermal energy with ambient environment of the lighting array.

6. The apparatus of claim 5 wherein the heat reservoir is a finned heat sink.

7. The apparatus of claim 6 wherein forced air is used to facilitate thermal transfer of energy from the finned heat sink to the ambient environment.

8. The apparatus of claim 5 wherein the heat reservoir is a cavity-filled structure capable of supporting fluid flow which, in turn, facilitates thermal transfer of energy from the heat reservoir to the ambient environment.

9. An apparatus comprising:
a lighting array for selectively illuminating a viewing area comprising,
a plurality of individual light emitting elements formed of a semiconductor compound which directly converts a percentage of electrons which are conducted through their volume into emitted photons in one of UV, visible, and IR portions of an electromagnetic spectrum, the light emitting elements being placed within a one- or two-dimensional pattern wherein element spacing is less than or equal to 0.05",
an electrically insulative, thermally conductive support substrate upon which the light emitting elements are attached in formation of the pattern, said support substrate specifically selected for its ability to facilitate conduction of locally generated thermal energy away from the light emitting elements while at the same time providing a sufficient degree of electrical isolation required to support parallel and series circuit construction associated with the individual light-emitting elements, and,
a heat dissipater disposed in direct thermal contact with the thermally conductive support substrate reducing the temperature of the light-emitting elements within the array;
a camera for acquiring images of specimens disposed in the illuminated viewing area;
a lighting control unit in communication with the lighting array; and,
a computer in communication with the camera to receive the acquired images and in communication with the lighting control unit.

10. The apparatus of claim 9 wherein optical radiation fields emitted by the plurality of individual light emitting elements are used, in either transmission and/or reflection, within systems performing on-line process control and/or machine vision inspection applications.

11. The apparatus of claim 10 wherein at least one of intensity, illumination geometry, spectral content, angular distribution and relative uniformity associated with the emitted optical radiation fields are controlled in order to optimize the resultant illumination for a selected machine vision inspection or process control application.

12. The apparatus of claim 11 further comprising a macro lens to direct light generated by the plurality of individual light emitting elements as a whole to a preselected area.

13. The apparatus of claim 12 wherein the macro lens utilizes at least one of refraction, reflection, and diffraction to induce desired lensing action.

14. The apparatus of claim 12 further comprising a diffuser element to direct light emitted by the plurality of individual light emitting elements to a preselected area.

15. The apparatus of claim 14 wherein the diffuser element is a Lambertian-type diffuser.

16. The apparatus of claim 14 if wherein the diffuser element is a diffractive-type diffuser generating either circular or elliptical illumination patterns.

17. The apparatus of claim 11 further comprising a plurality of lenses arranged as a lenslet array to direct light generated by the plurality of individual light emitting elements to a preselected area.

18. The apparatus of claim 17 wherein individual elements of the lenslet array utilize at least one of refraction, reflection, and diffraction to induce the desired lensing action.

19. The apparatus of claim 17 further comprising a diffuser element to direct light emitted by the plurality of individual light emitting elements to a preselected area.

20. The apparatus of claim 19 wherein the diffuser element is a Lambertian-type diffuser.

21. The apparatus of claim 19 wherein the diffuser element is a diffractive-type diffuser generating either circular or elliptical illumination patterns.

22. The apparatus of claim 11 further comprising a diffuser element to direct light emitted by the plurality of individual light emitting elements to a preselected area.

23. The apparatus of claim 22 wherein the diffuser element is a Lambertian-type diffuser.

24. The apparatus of claim 22 wherein the diffuser element is a diffractive-type diffuser generating either circular or elliptical illumination patterns.

25. The apparatus of claim 11 wherein at least one of pulse duration and period and drive current associated with the array are electronically configurable to optimize the emitted optical radiation fields for a selected application.

26. The apparatus of claim 25 wherein the plurality of individual light emitting elements are operated in a pulsed-current mode.

27. The apparatus of claim 26 wherein the pulse duration and period are electronically configurable parameters.

28. The apparatus of claim 26 wherein the drive current to the lighting elements is an electronically configurable parameter.

29. The apparatus of claim 26 further comprising varying geometric areas within the array which are independently addressable as a function of the drive current and the pulse duration.

30. The apparatus of claim 29 wherein each of the plurality of light emitting elements emit optical radiation of essentially the same limited wavelength range so that an electronic control unit provides the array with a configurable intensity and geometry capability to optimize the emitted radiation fields for a selected application area.

31. The apparatus of claim 29 wherein elements of the plurality of individual light emitting elements of two or more emission wavelengths are contained within the array so that an electronic control unit provides the array with a configurable intensity, geometry, and spectral content capability to optimize the emitted radiation fields for a selected application area.

32. The apparatus of claim 25 wherein the plurality of individual light emitting elements are operated in a continuous-current mode.

33. The apparatus of claim 32 wherein the drive current to the plurality of individual light emitting elements is an electronically configurable parameter.

34. The apparatus of claim 32 further comprising varying geometrical areas within the array which are independently addressable as a function of the drive current.

35. The apparatus of claim 34, wherein each of the individual light emitting elements emit optical radiation of essentially the same limited wavelength range so that an electronic control unit provides the array with a configurable intensity and geometry capability to optimize the emitted radiation fields for a selected application area.

36. The apparatus of claim 34 wherein elements of the plurality of light emitting elements of two or more emission wavelengths are contained within the array so that an electronic control unit provides the array with a configurable intensity, geometry, and spectral content capability to optimize the emitted radiation fields for a selected application area.

37. A method of performing machine vision and/or process control operations, the method comprising steps of:

providing a camera to be positioned to view specimens in a viewing area;

providing a plurality of individual light emitting elements formed of a semiconductor compound which directly converts a percentage of electrons which are conducted through their volume into emitted photons in one of UV, visible, and IR portions of an electromagnetic spectrum;

arranging the plurality of light emitting elements in a pattern wherein element spacing is less than or equal to 0.05" on an electronically insulative, thermally conductive support substrate;

implementing the arranged array as a light source;

illuminating the viewing area with the arranged array;

conducting locally generated thermal energy away from the light emitting elements by the support substrate to a heat dissipater disposed in direct thermal contact with the thermally conductive support substrate for reducing the temperature of the light-emitting elements within the array;

acquiring images of the specimens in the viewing area by the camera; and transmitting the acquired images to a computer.

* * * * *